United States Patent
Simonin

(10) Patent No.: US 11,241,312 B2
(45) Date of Patent: Feb. 8, 2022

(54) MEDICAL DEVICE DELIVERY SYSTEM INCLUDING A RESISTANCE MEMBER

(71) Applicant: BOSTON SCIENTIFIC SCIMED, INC., Maple Grove, MN (US)

(72) Inventor: Pierre Simonin, Montflovin (FR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 119 days.

(21) Appl. No.: 16/709,305

(22) Filed: Dec. 10, 2019

(65) Prior Publication Data

US 2020/0179117 A1 Jun. 11, 2020

Related U.S. Application Data

(60) Provisional application No. 62/777,487, filed on Dec. 10, 2018.

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/2433* (2013.01);
(Continued)

(58) Field of Classification Search
CPC .... A61F 2/2436; A61F 2/2418; A61F 2/2433; A61F 2/9522; A61F 2/9517; A61F 2240/001; A61F 2250/0098
See application file for complete search history.

(56) References Cited

U.S. PATENT DOCUMENTS

| 15,192 A | 6/1856 | Peale |
|---|---|---|
| 2,682,057 A | 6/1954 | Lord |
| (Continued) | | |

FOREIGN PATENT DOCUMENTS

| AU | 2002329324 B2 | 7/2007 |
|---|---|---|
| CN | 1338951 A | 3/2002 |
| (Continued) | | |

OTHER PUBLICATIONS

US 8,062,356 B2, 11/2011, Salahieh et al. (withdrawn)
(Continued)

*Primary Examiner* — Melanie R Tyson
*Assistant Examiner* — Andrew P. Restaino
(74) *Attorney, Agent, or Firm* — Seager, Tufte & Wickhem LLP

(57) ABSTRACT

Example medical device delivery systems are disclosed. An example delivery system for an implantable medical device includes an outer shaft having a distal end region, a proximal end region and a lumen extending therebetween. The delivery system also includes a handle coupled to the proximal end region of the outer shaft, wherein the handle includes a first actuator, a carriage and a housing. The delivery system also includes a selector coupled to the handle and a resistance member disposed along a portion of the selector. Further, the selector is configured to shift between a first configuration and a deployment configuration. Additionally, the carriage is free from the resistance member in the first configuration and the resistance member contacts the carriage in the deployment configuration.

18 Claims, 13 Drawing Sheets

(52) U.S. Cl.
CPC ............ *A61F 2/9517* (2020.05); *A61F 2/9522* (2020.05); *A61F 2240/001* (2013.01); *A61F 2250/0098* (2013.01)

(56) References Cited

U.S. PATENT DOCUMENTS

| | | |
|---|---|---|
| 2,701,559 A | 2/1955 | Cooper |
| 2,832,078 A | 4/1958 | Williams |
| 3,029,819 A | 4/1962 | Starks |
| 3,099,016 A | 7/1963 | Lowell |
| 3,113,586 A | 12/1963 | Edmark |
| 3,130,418 A | 4/1964 | Head et al. |
| 3,143,742 A | 8/1964 | Cromie |
| 3,221,006 A | 11/1965 | Moore et al. |
| 3,334,629 A | 8/1967 | Cohn |
| 3,365,728 A | 1/1968 | Edwards et al. |
| 3,367,364 A | 2/1968 | Cruz et al. |
| 3,409,013 A | 11/1968 | Henry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten et al. |
| 4,662,885 A | 5/1987 | DiPisa |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz et al. |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Faheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,739 A | 6/1995 | Jessen |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,469,868 A | 11/1995 | Reger |

(56) References Cited

U.S. PATENT DOCUMENTS

| | | |
|---|---|---|
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,489,297 A | 2/1996 | Duran |
| 5,500,014 A | 3/1996 | Quijano et al. |
| 5,507,767 A | 4/1996 | Maeda et al. |
| 5,522,881 A | 6/1996 | Lentz |
| 5,534,007 A | 7/1996 | Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,784 A | 5/1997 | Strecker |
| 5,645,559 A | 7/1997 | Hachtman et al. |
| 5,653,745 A | 8/1997 | Trescony et al. |
| 5,662,671 A | 9/1997 | Barbut et al. |
| 5,667,523 A | 9/1997 | Bynon et al. |
| 5,674,277 A | 10/1997 | Freitag |
| 5,681,345 A | 10/1997 | Euteneuer |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,772,609 A | 6/1998 | Nguyen et al. |
| 5,776,188 A | 7/1998 | Shepherd et al. |
| 5,782,904 A | 7/1998 | White et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,015,431 A | 1/2000 | Thornton et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson et al. |
| 6,051,014 A | 4/2000 | Jang |
| 6,059,827 A | 5/2000 | Fenton |
| 6,074,418 A | 6/2000 | Buchanan et al. |
| 6,093,203 A | 7/2000 | Uflacker |
| 6,096,074 A | 8/2000 | Pedros |
| 6,110,198 A | 8/2000 | Fogarty et al. |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,911 B1 | 3/2001 | Milo |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,309,417 B1 | 10/2001 | Spence et al. |
| 6,312,465 B1 | 11/2001 | Griffin et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | Paulis |
| 6,352,708 B1 | 3/2002 | Duran et al. |

(56) References Cited

U.S. PATENT DOCUMENTS

| | | |
|---|---|---|
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,387,122 B1 | 5/2002 | Cragg |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B2 | 1/2003 | Pavcnik et al. |
| 6,527,800 B1 | 3/2003 | McGuckin et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,540,782 B1 | 4/2003 | Snyders |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,729,356 B1 | 5/2004 | Baker et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | Germain et al. |
| 6,769,434 B2 | 8/2004 | Liddicoat et al. |
| 6,773,454 B2 | 8/2004 | Wholey et al. |
| 6,773,456 B1 | 8/2004 | Gordon et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,814,754 B2 | 11/2004 | Greenhalgh |
| 6,821,297 B2 | 11/2004 | Snyders |
| 6,824,041 B2 | 11/2004 | Grieder et al. |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 6,989,027 B2 | 1/2006 | Mien et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |
| 7,147,663 B1 | 12/2006 | Berg et al. |
| 7,166,097 B2 | 1/2007 | Barbut |
| 7,175,652 B2 | 2/2007 | Cook et al. |
| 7,175,653 B2 | 2/2007 | Gaber |

(56) References Cited

U.S. PATENT DOCUMENTS

| | | |
|---|---|---|
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,712,606 B2 | 5/2010 | Salahieh et al. |
| 7,722,638 B2 | 5/2010 | Deyette et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,172,896 B2 | 5/2012 | McNamara et al. |
| 8,182,528 B2 | 5/2012 | Salahieh et al. |
| 8,192,351 B2 | 6/2012 | Fishier et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,647,381 B2 | 2/2014 | Essinger et al. |
| 8,668,733 B2 | 3/2014 | Haug et al. |
| 8,696,743 B2 | 4/2014 | Holecek et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 9,168,131 B2 | 10/2015 | Yohanan et al. |
| 9,216,082 B2 | 12/2015 | Von Segesser et al. |
| 9,333,075 B2 | 5/2016 | Biadillah et al. |
| 9,414,915 B2 | 8/2016 | Lombardi et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0027338 A1 | 10/2001 | Greenberg |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055774 A1 | 5/2002 | Liddicoat |
| 2002/0058987 A1 | 5/2002 | Butaric et al. |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0156522 A1 | 10/2002 | Ivancev et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |

(56) References Cited

U.S. PATENT DOCUMENTS

| | | |
|---|---|---|
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0074058 A1 | 4/2003 | Sherry |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0165352 A1 | 9/2003 | Ibrahim et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204249 A1 | 10/2003 | Letort |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2003/0236567 A1 | 12/2003 | Elliot |
| 2004/0019374 A1 | 1/2004 | Hojeibane et al. |
| 2004/0033364 A1 | 2/2004 | Spiridigliozzi et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |

(56) References Cited

U.S. PATENT DOCUMENTS

| | | |
|---|---|---|
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025857 A1 | 2/2006 | Bergheim et al. |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0216312 A1 | 8/2009 | Straubinger et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2010/0004730 A1* | 1/2010 | Benjamin ............ A61F 2/95 623/1.11 |
| 2010/0036479 A1 | 2/2010 | Hill et al. |
| 2010/0049313 A1 | 2/2010 | Alon et al. |
| 2010/0082089 A1 | 4/2010 | Quadri et al. |
| 2010/0094399 A1 | 4/2010 | Dorn et al. |
| 2010/0121434 A1 | 5/2010 | Paul et al. |
| 2010/0161045 A1 | 6/2010 | Righini |
| 2010/0185275 A1 | 7/2010 | Richter et al. |
| 2010/0191320 A1 | 7/2010 | Straubinger et al. |
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0280495 A1 | 11/2010 | Paul et al. |
| 2010/0298931 A1 | 11/2010 | Quadri et al. |
| 2011/0257735 A1 | 10/2011 | Salahieh et al. |
| 2011/0264196 A1 | 10/2011 | Savage et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2011/0307049 A1 | 12/2011 | Kao |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0179244 A1 | 7/2012 | Schankereli et al. |
| 2012/0197379 A1 | 8/2012 | Laske et al. |
| 2012/0271398 A1 | 10/2012 | Essinger et al. |
| 2012/0303113 A1 | 11/2012 | Benichou et al. |
| 2012/0303116 A1 | 11/2012 | Gorman et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030519 A1 | 1/2013 | Tran et al. |
| 2013/0030520 A1 | 1/2013 | Lee et al. |
| 2013/0079867 A1 | 3/2013 | Hoffman et al. |
| 2013/0079869 A1 | 3/2013 | Straubinger et al. |
| 2013/0096664 A1 | 4/2013 | Goetz et al. |
| 2013/0123796 A1 | 5/2013 | Sutton et al. |
| 2013/0138207 A1 | 5/2013 | Quadri et al. |
| 2013/0158656 A1 | 6/2013 | Sutton et al. |
| 2013/0184813 A1 | 7/2013 | Quadri et al. |
| 2013/0190865 A1 | 7/2013 | Anderson |
| 2013/0231736 A1 | 9/2013 | Essinger et al. |
| 2013/0304199 A1 | 11/2013 | Sutton et al. |
| 2014/0018911 A1 | 1/2014 | Zhou et al. |
| 2014/0039614 A1 | 2/2014 | Delaloye et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0200649 A1 | 7/2014 | Essinger et al. |
| 2014/0243967 A1 | 8/2014 | Salahieh et al. |
| 2014/0330219 A1* | 11/2014 | Quint ............... A61F 2/2427 604/264 |
| 2015/0012085 A1 | 1/2015 | Salahieh et al. |
| 2015/0018938 A1 | 1/2015 | Von Segesser et al. |
| 2015/0073540 A1 | 3/2015 | Salahieh et al. |
| 2015/0073541 A1 | 3/2015 | Salahieh et al. |
| 2015/0127094 A1 | 5/2015 | Salahieh et al. |

(56) References Cited

U.S. PATENT DOCUMENTS

| | | |
|---|---|---|
| 2015/0245934 A1 | 9/2015 | Lombardi et al. |
| 2015/0297381 A1 | 10/2015 | Essinger et al. |
| 2015/0305863 A1* | 10/2015 | Gray .............. A61F 2/2436 623/2.11 |
| 2015/0366665 A1 | 12/2015 | Lombardi et al. |
| 2016/0038281 A1 | 2/2016 | Delaloye et al. |
| 2016/0045307 A1 | 2/2016 | Yohanan et al. |
| 2016/0058434 A1 | 3/2016 | Delaloye et al. |
| 2016/0193047 A1 | 7/2016 | Delaloye et al. |
| 2016/0199184 A1 | 7/2016 | Ma et al. |
| 2016/0228249 A1 | 8/2016 | Mantanus et al. |
| 2016/0262884 A1 | 9/2016 | Lombardi et al. |
| 2017/0035568 A1 | 2/2017 | Lombardi et al. |
| 2017/0224486 A1 | 8/2017 | Delaloye et al. |
| 2018/0161064 A1 | 6/2018 | Fitterer et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 579523 A1 | 1/1994 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 0937439 B1 | 9/2003 |
| EP | 1340473 A2 | 9/2003 |
| EP | 1356793 A3 | 3/2004 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1469797 A1 | 10/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1690515 A1 | 8/2006 |
| EP | 1605871 B1 | 7/2008 |
| EP | 2047824 B1 | 5/2012 |
| EP | 2749254 B1 | 6/2015 |
| EP | 2926766 A1 | 10/2015 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9951165 A1 | 10/1999 |
| WO | 0009059 A2 | 2/2000 |
| WO | 2000009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106959 A1 | 2/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 2001054625 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 8/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A1 | 2/2003 |
| WO | 03028592 A1 | 4/2003 |
| WO | 03030776 A2 | 4/2003 |
| WO | 03032869 A1 | 4/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03094793 A1 | 11/2003 |
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019817 A1 | 3/2004 |
| WO | 2004021922 A2 | 3/2004 |
| WO | 2004023980 A2 | 3/2004 |
| WO | 2004019811 A9 | 4/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |

(56) References Cited

FOREIGN PATENT DOCUMENTS

| | | |
|---|---|---|
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2005062980 A3 | 5/2006 |
| WO | 2006093795 A1 | 9/2006 |
| WO | 2006138391 A2 | 12/2006 |
| WO | 2007009117 A1 | 1/2007 |
| WO | 2007033093 A2 | 3/2007 |
| WO | 2007035471 A2 | 3/2007 |
| WO | 2005102015 A3 | 4/2007 |
| WO | 2007044285 A2 | 4/2007 |
| WO | 2007058847 A2 | 5/2007 |
| WO | 2007092354 A2 | 8/2007 |
| WO | 2007097983 A2 | 8/2007 |
| WO | 2007053243 A2 | 9/2007 |
| WO | 2008028569 A1 | 3/2008 |
| WO | 2008035337 A2 | 3/2008 |
| WO | 2010042950 A2 | 4/2010 |
| WO | 2010098857 A1 | 9/2010 |
| WO | 2012116368 A2 | 8/2012 |
| WO | 2012162228 A1 | 11/2012 |
| WO | 2013009975 A1 | 1/2013 |
| WO | 2013028387 A2 | 2/2013 |
| WO | 2013074671 A1 | 5/2013 |
| WO | 2013096545 A1 | 6/2013 |
| WO | 2016126511 A2 | 8/2016 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Carpentier-Edwards PERIMOUNT Bioprosthesis (2003).
International Search Report and Written Opinion dated Oct. 22, 2018 for International Application No. PCT/US2018/044318.
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EP Patent Office, EP Application No. 04813777.2, dated Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in the aorta and the beating heart of closed chest pigs (Abstract)." Eur. Heart J., 11 (SuppL): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502 Technical Design Report. Northeastern University, pp. 1-93, Nov. 5, 2007.
Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent-Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
Dake et al., "Transluminal Placement of Endovascular Stent-Grafts for the Treatment of Descending Thoracic Aortic Aneurysms." New Engl. J of Med., 331(26):1729-34 (1994).
Dalby et al., "Non-Surgical Aortic Valve Replacement" Br. J. Cardiol., 10:450-2 (2003).

(56) References Cited

OTHER PUBLICATIONS

Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Dotter, "Transluminally-Placed Coilspring Endarterial Tube Grafts," Investigative Radiology, pp. 329-332 (1969).
Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference Sep. 5, 2000.
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am Heart J., 142(3): 476-481, Sep. 2001.
Lawrence et al., "Percutaneous Endovascular Graft: Experimental Evaluation," Radiology, 163(2): 357-60 (May 1987).
Levi et al., "Future of Interventional Cardiology in Pediactrics." Current Opinion in Cardiol., 18:79-90 (2003).
Levy, "*Mycobacterium chelonei* Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.

Magovern et al., "Twenty-five-Year Review of the Magovern-Cromie Sutureless Aortic Valve." Ann. Thorac. Surg., 48: S33-4 (1989).
Maraj et al., Evaluation of Hemolysis in Patients with Prosthetic Heart Valves, Clin. Cardiol. 21, 387-392 (1998).
Mckay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Grafts for Aortic Aneurysms: Feasibility Study." Radiology, 170: 1033-1037(1989).
Moazami et al., "Transluminal Aortic Valve Placement: A Feasibility Study With a Newly Designed Collapsiable Aortic Valve," ASAIO J vol. 42:5, pp. M383-85 (Sep./Oct. 1996).
Moulopoulos et al., "Catheter-Mounted Aortic Valves." Annals of Thoracic Surg., 11 (5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vasc. Surg., 5 (6):491-9 (1991).
Pavcnik et al., "Percutaneous Bioprosthetic Venous Valve: A Long-term Study in Sheep." J. of Vascular Surg., 35(3): 598-603, Mar. 2002.
Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Printz, et al., "Let the Blood Circulate." Sulzer Tech. Rev. 4/99.
U.S. Appl. No. 60/553,945 to White.
Raillat et al., "Treatment of Iliac Artery Stenosis with the Wallstent Endoprosthesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc. Intervent. Radiol. 15: 319-327 (1992).
Schurink et al,. "Stent Attachment Site-related Endoleakage after Stent Graft Treatment: An in vitro study of the effects of graft size, stent type, and atherosclerotic wall changes" J. Vasc. Surg., 30(4):658-67 (Oct. 1999).
Seminars in Interventional Cardiology, ed. P.W. Surruys, vol. 5 (2000).
Sochman et al., "Percutaneous Transcatheter Aortic Disc Valve Prosthesis Implantation: A Feasibility Study." Cardiovasc. Intervent Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience " J. Endovasc. Ther. 8:457-464 (2001).
Thompson et al., "Endoluminal stent grafting of the thoracic aorta: Initial experience with the Gore Excluder," Journal of Vascular Surgery, 1163-70 (Jun. 2002).
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. 9-17, Feb. 2004.
Supplemental Search Report from EP Patent Office, EP Application No. 04815634.3, dated Aug. 19, 2011.
Supplemental Search Report from EP Patent Office, EP Application No. 05758878.2, dated Oct. 24, 2011.
Textbook of Interventional Cardiology, 2d Ed., Chapter 75: Percutaneous Expandable Prosthetic Valves (1994).

(56) References Cited

OTHER PUBLICATIONS

Stassano, "Mid-term Results of the Valve on Valve Technique for Bioprosthetic failure." European journal of Ccardiothoracic Surgery:vol 18, 453-457, Oct. 2000.
Topol, "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
VentureBeatProfiles, Claudio Argento, Jan. 7, 2010, http://venturebeatprofiles.com/person/profile/claudio-argento.
Vossoughi et al.. Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).
USPTO Case IPR2017-01293, U.S. Pat. No. 8,992,608 B, Oct. 13, 2017.
Zhou et al., "Self-expandable Valved Stent of Large Size: Off-Bypass Implantation in Pulmonary Position." Eur. J. Cardiothorac, 24: 212-216, Aug. 2003.
Gore Excluder Instructions for Use (2002).
USPTO Case IPR2016-__, U.S. Pat. No. 8,992,608 "Petition for Interpartes Review of U.S. Pat. No. 8,992,608" Oct. 12, 2016.
USPTO Case IPR 2017-0006, U.S. Pat. No. 8,992,608 B2, "Final Written Decision" dated Mar. 23, 2018.
Fluency Vascular Stent Graft Instructions for Use (2003).
International Search Report and Written Opinion dated Mar. 18, 2020 for International Application No. PCT/US2019/065454.

\* cited by examiner

MEDICAL DEVICE DELIVERY SYSTEM INCLUDING A RESISTANCE MEMBER

CROSS-REFERENCE TO RELATED APPLICATIONS

This application claims the benefit of priority to U.S. Provisional Application Ser. No. 62/777,487, filed Dec. 10, 2018, the entirety of which is incorporated herein by reference.

TECHNICAL FIELD

The present disclosure pertains to medical devices, and methods for manufacturing medical devices. More particularly, the present disclosure pertains to medical device delivery systems including a translating engagement member.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example delivery system for an implantable medical device includes an outer shaft having a distal end region, a proximal end region and a lumen extending therebetween. The delivery system also includes a handle coupled to the proximal end region of the outer shaft, wherein the handle includes a first actuator, a carriage and a housing. The delivery system also includes a selector which may be in the form of a cap coupled to the handle and a resistance member disposed along a portion of the selector. Further, the selector is configured to shift between a first configuration and deployment configuration. Additionally, the carriage is free from the resistance member in the first configuration and the resistance member contacts the carriage in the deployment configuration.

Alternatively or additionally to any of the embodiments above, wherein the resistance member contacts an inner surface along a distal end region of the housing in the first configuration.

Alternatively or additionally to any of the embodiments above, wherein the resistance member contacts an inner surface along a distal end region of the carriage in the deployment configuration.

Alternatively or additionally to any of the embodiments above, wherein the carriage is configured to rotate, and wherein the resistance member is configured to increase a rotational force required to rotate the carriage in the deployment configuration.

Alternatively or additionally to any of the embodiments above, wherein the cap includes a circumferential groove positioned along a proximal end region thereof, wherein at least a portion of the resistance member is positioned along the groove.

Alternatively or additionally to any of the embodiments above, further comprising an implant loading device positioned adjacent the distal end region of the outer shaft.

Alternatively or additionally to any of the embodiments above, wherein the cap includes an inner surface, an outer surface and a wall extending therebetween, and wherein the cap includes an aperture extending through a wall of the cap.

Alternatively or additionally to any of the embodiments above, wherein the aperture includes a length, and wherein the length of the aperture corresponds to a distance along which the cap shifts between the first configuration and the deployment configuration.

Alternatively or additionally to any of the embodiments above, wherein the aperture is aligned along a longitudinal axis of the cap.

Alternatively or additionally to any of the embodiments above, wherein the aperture is offset from a longitudinal axis of the cap.

Alternatively or additionally to any of the embodiments above, wherein rotating the cap shifts it between the first configuration and the deployment configuration.

Alternatively or additionally to any of the embodiments above, wherein the cap includes a circumferential lip extending circumferentially along a distal end region thereof.

Alternatively or additionally to any of the embodiments above, wherein the lip extends radially away from an outer surface of the cap.

Alternatively or additionally to any of the embodiments above, wherein the resistance member is configured to exert a radially outward force on an inner surface of the carriage in the deployment configuration.

Another example delivery system for an implantable medical device includes:
an outer shaft having a distal end region, a proximal end region and a lumen extending therebetween;
a handle coupled to the proximal end region of the outer shaft, wherein the handle includes a first actuator, a carriage and a housing;
a cap coupled to the handle; and
a resistance member disposed along a portion of the cap;
wherein the cap is configured to shift between a first configuration and a deployment configuration, and wherein the carriage is free from the resistance member in the first configuration and wherein the resistance member exerts a radially outward force upon the carriage in the deployment configuration.

Alternatively or additionally to any of the embodiments above, wherein the resistance member contacts an inner surface along a distal end region of the housing in the first configuration.

Alternatively or additionally to any of the embodiments above, wherein the resistance member contacts an inner surface along a distal end region of the carriage in the deployment configuration.

Alternatively or additionally to any of the embodiments above, wherein the carriage is configured to rotate, and wherein the resistance member is configured to increase a rotational force required to rotate the carriage in the deployment configuration.

An example method of manufacturing an implantable medical device includes:
engaging the implantable medical device with a medical device delivery system in a pre-deployment configuration, the medical device delivery system including:

an outer shaft having a distal end region, a proximal end region and a lumen extending therebetween;
a handle coupled to the proximal end region of the outer shaft, wherein the handle includes a first actuator, a carriage and a housing;
a cap coupled to the handle; and
a resistance member disposed along a portion of the cap;
converting the medical device delivery system from a pre-deployment configuration to a deployment configuration, wherein converting the medical device delivery system includes shifting the cap from a first position to a second position, wherein the carriage is free from the resistance member when the cap is in the first position and wherein the resistance member contacts the carriage when the cap is in the second position.

Alternatively or additionally to any of the embodiments above, wherein the implantable medical device includes an implantable heart valve.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
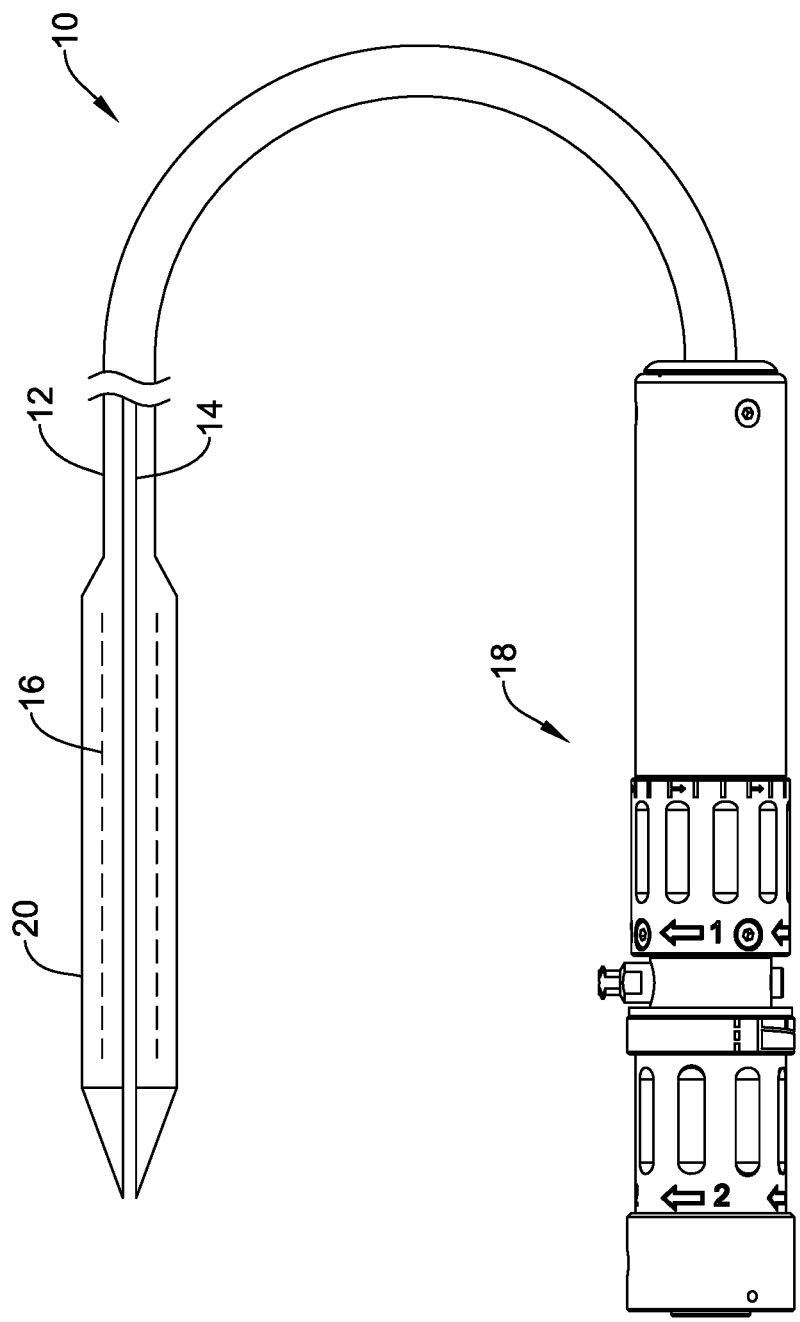
FIG. 1 illustrates an example medical device delivery system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health conditions and/or death if not dealt with properly. Treatment of defective heart valves poses other challenges in that the treatment often requires the repair or outright replacement of the defective valve. Such therapies may be highly invasive to the patient. Disclosed herein are medical devices that may be used to deliver a medical device to a portion of the cardiovascular system in order to diagnose, treat, and/or repair the system. At least some of the medical devices disclosed herein may be used to deliver a replacement heart valve (e.g., a replacement aortic valve, replacement mitral valve, etc.). In addition, the devices disclosed herein may deliver the replacement heart valve percutaneously and, thus, may be much less invasive to the patient.

The devices disclosed herein may also provide additional benefits as described in more detail below.

The figures illustrate selected components and/or arrangements of a medical device system 10, shown schematically in FIG. 1, for example. It should be noted that in any given figure, some features of the medical device system 10 may not be shown, or may be shown schematically, for simplicity. Additional details regarding some of the components of the medical device system 10 may be illustrated in other figures in greater detail.

The medical device system 10 may be used to deliver and/or deploy a variety of medical devices to a number of locations within the anatomy. In at least some embodiments, the medical device system 10 may include a replacement heart valve delivery system (e.g., a replacement aortic valve delivery system) that can be used for percutaneous delivery of a medical implant 16, such as a replacement/prosthetic heart valve. This, however, is not intended to be limiting as the medical device system 10 may also be used for other interventions including valve repair, valvuloplasty, delivery of an implantable medical device (e.g., such as a stent, graft, etc.), and the like, or other similar interventions.

The medical device system 10 may generally be described as a catheter system that includes an outer shaft 12, an inner shaft 14 (a portion of which is shown in FIG. 1) extending at least partially through a lumen of the outer shaft 12, and a medical implant 16 (e.g., a replacement heart valve implant) which may be coupled to the inner shaft 14 and disposed within an implant containment region 20 coupled to the outer shaft 12, the inner shaft 14 or both the outer shaft 12 and the inner shaft 14 during delivery of the medical implant 16. In some embodiments, a medical device handle 18 may be disposed at a proximal end of the outer shaft 12 and/or the inner shaft 14 and may include one or more actuation mechanisms associated therewith. In other words, a tubular member (e.g., the outer shaft 12, the inner shaft 14, etc.) may extend distally from the medical device handle 18. As will be described in greater detail below, the medical device handle 18 may be designed to manipulate the position of the outer shaft 12 relative to the inner shaft 14 and/or aid in the deployment of the medical implant 16.

In use, the medical device system 10 may be advanced percutaneously through the vasculature to a position adjacent to an area of interest and/or a treatment location. For example, in some embodiments, the medical device system 10 may be advanced through the vasculature to a position adjacent to a defective native valve (e.g., aortic valve, mitral valve, etc.). Alternative approaches to treat a defective aortic valve and/or other heart valve(s) are also contemplated with the medical device system 10. During delivery, the medical implant 16 may be generally disposed in an elongated and low profile "delivery" configuration within the implant containment region 20, as seen schematically in FIG. 1 for example. Once positioned, the outer shaft 12 and/or inner shaft 14 may be translated relative to each other and/or the medical implant 16 to expose (e.g., deploy) the medical implant 16. In some instances, a portion of the medical implant 16 may be self-expanding such that exposure of the medical implant 16 may deploy the medical implant 16. Alternatively, the medical implant 16 may be manipulated using the medical device handle 18 in order to translate the medical implant 16 into a deployed configuration suitable for implantation within the anatomy. When the medical implant 16 is suitably deployed within the anatomy, the medical device system 10 may be disconnected, detached, and/or released from the medical implant 16 and the medical device system 10 can be removed from the vasculature, leaving the medical implant 16 at the target tissue site.

As discussed above, the medical device system 10 may comprise an implant containment region 20 for accommodating the medical implant 16 in a collapsed form for introduction into the anatomy. The medical implant 16 may be a cardiac stent-valve. The delivery system 10 may be configured to permit delivery of the stent-valve 16 to a target site of implantation while the heart remains beating, for example, using a minimally invasive surgical and/or percutaneous procedure. In some embodiments, the delivery system 10 may be configured for introduction into the anatomical vascular system, and for advancement along the vasculature system to the desired site of implantation. For example, the delivery system 10 may be configured for introduction into the femoral artery, and guided retrograde via the descending aorta, aortic arch, and ascending aorta to the heart (sometimes called a transfemoral access). In other embodiments, the delivery system 10 may be insertable via the subclavian artery and guided retrograde to the heart (sometimes call transsubclavian access). In other embodiments, the delivery system 10 may be inserted directly into a chamber of the heart such as a ventricle (for example, left ventricle) via a direct access route while the heart remains beating. For example, a direct access route may be through an aperture opened in the apex of the heart (sometimes called a transapical access).

It can be appreciated that during delivery and/or deployment of an implantable medical device (e.g., the medical implant 16), portions of the medical device system 10 may be required to be advanced through tortuous and/or narrow body lumens. Therefore, it may be desirable to utilize components and design medical delivery systems (e.g., such as the medical device system 10 and/or other medical devices) that reduce the profile of portions of the medical device while maintaining sufficient strength (compressive, torsional, etc.) and flexibility of the system as a whole.

In some examples, the stent-valve 16 may be expandable from a compressed or collapsed condition to an expanded condition, in order to anchor the stent-valve 16 at the implantation site. For example, the stent-valve 16 may form a friction and/or interference fit with respect to the native anatomy. Various shapes and geometries of stent-valve 16 may be used to fit the anatomy at the site of implantation. The stent-valve 16 may be self-expanding and/or may be configured to be expandable by an expandable member (for example, a balloon). Self-expanding stent-valves 16 may be constructed from shape-memory material, for example, a shape-memory metal alloy (e.g., nitinol). The self-expanding stent-valve 16 may be retained in its compressed state by being constrained within the containment region 20 of the delivery system 10. Upon at least partial release from the containment region 20, the released portion of the stent-valve 16 may be free to expand. Balloon expandable stent-valves 16 may also be made of shape-memory material, stainless steel, cobalt-chromium alloy or other materials. A non-limiting list of materials contemplated for one or more components of the stent delivery system 10 described herein is set forth below.

Figure 2:
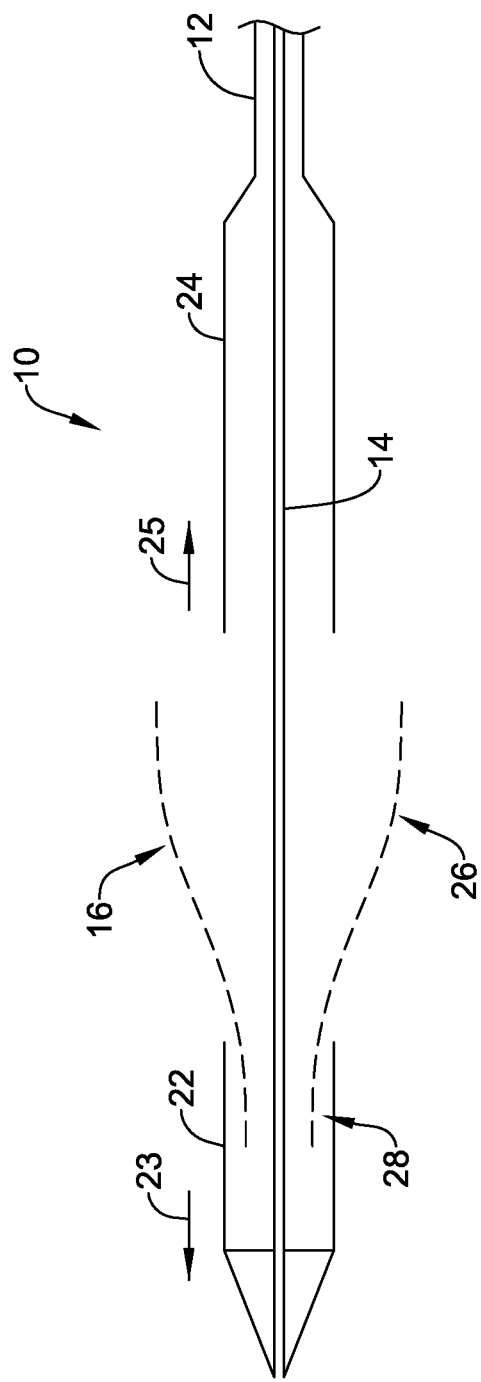
FIG. 2 illustrates an example step in the deployment of the example medical device shown in FIG. 1.
Figure 3:
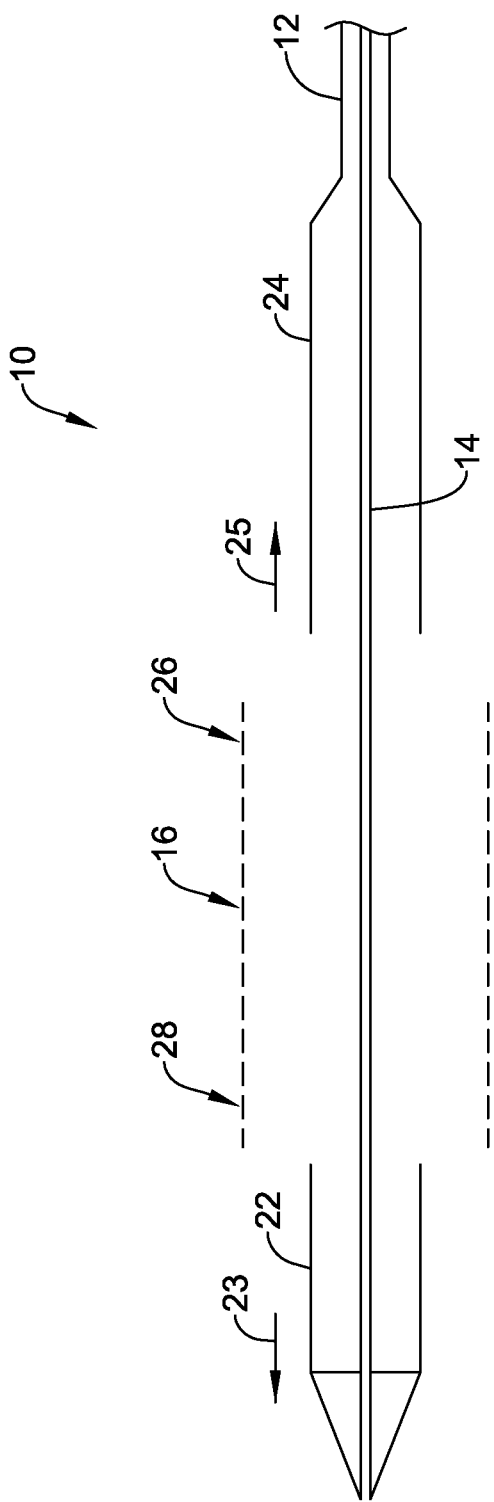
FIG. 3 illustrates another example step in the deployment of the example medical device shown in FIG. 1.

FIG. 2 illustrates an example first step in releasing (e.g., deploying) the stent-valve 16 from the medical device delivery system 10. As shown in FIG. 2, the containment region 20 of the medical device delivery system 10 may comprise a first sheath 22 and/or a second sheath 24. The first sheath 22 may be referred to as the distal sheath. The second sheath 24 may be referred to as the proximal sheath. Together, the first sheath 22 and the second sheath 24 may be translatable between a closed position (at least partially covering the stent-valve 16) and an open position (at least partially exposing at least a portion of the stent-valve 16). For example, FIG. 1 illustrates both the first sheath 22 and the second sheath 24 (collectively referred to as the containment region 20 above) in a closed position (wherein they are covering the stent-valve 16). Further, FIG. 2 illustrates that the first sheath 22 and the second sheath 24 may be translatable in opposite directions to an open position, as described above. For example, the first sheath 22 may be translatable in a distal direction (indicated by arrow 23 in FIG. 2) while the second sheath 24 may be translatable in a proximal direction (indicated by arrow 25 in FIG. 2).

Additionally, in some instances, the first sheath 22 and the second sheath 24 may translate independent of one another to release of the stent-valve 16 from the medical device delivery system 10. For example, FIG. 2 illustrates that translating the second sheath 24 in a proximal direction (e.g., indicated by arrow 25) while holding the first sheath 22 stationary, a portion 26 of the stent-valve 16 may be partially or fully released before a portion 28 of the stent-valve 16 covered by the first sheath 22 is partially or fully released. Further 3 illustrates that the portion 28 may subsequently be released by translation of the first sheath 22 in a distal direction (e.g., indicated by arrow 23).

Additionally, in some examples, the length of the second sheath 24 may be greater than the length of the first sheath 22. For example, the ratio of the second sheath 24 length divided by the first sheath 22 length may be at least 1.1, optionally at least 1.2, optionally at least 1.3, optionally at least 1.4, optionally at least 1.5, optionally at least 1.6, optionally at least 1.7, optionally at least 1.8, optionally at least 1.9, optionally at least 2.0, optionally at least 2.1, optionally at least 2.2, optionally at least 2.3, optionally at least 2.4, optionally at least 2.5, optionally at least 2.6, optionally at least 2.7, optionally at least 2.8, optionally at least 2.9, optionally at least 3, optionally at least 3.5, optionally at least 4 or optionally at least 4.5, or optionally at least 5.

Figure 4:
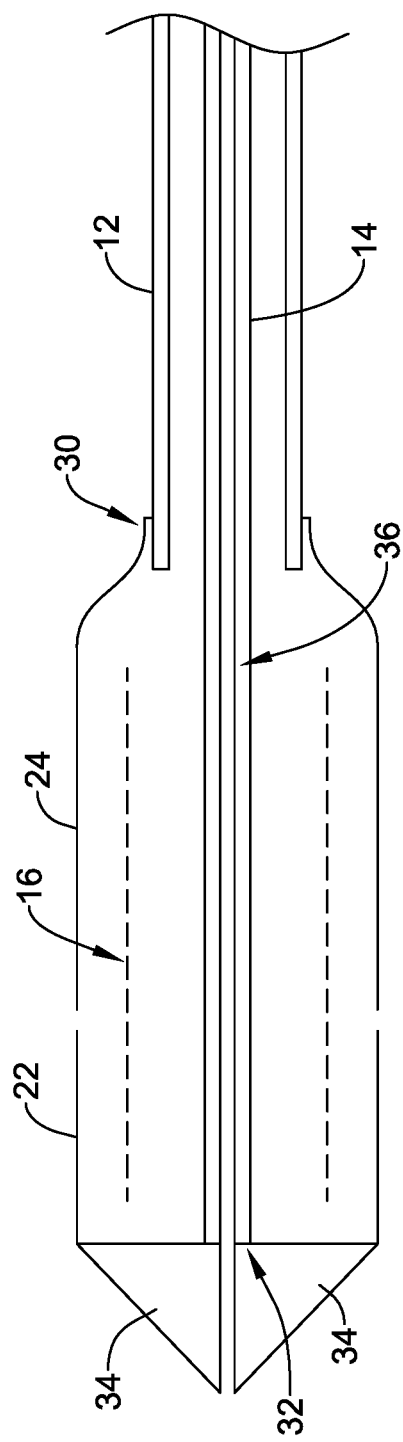
FIG. 4 illustrates a portion of the medical device system shown in FIGS. 1-3.

FIG. 4 shows an enlarged portion of the distal region of the medical device delivery system 10 described above. For example, FIG. 4 illustrates the outer shaft 12 attached to the second (e.g., proximal) sheath 24 at a first connection point 30. Additionally, FIG. 4 illustrates the inner shaft 14 attached to a tip member 34 at a second connection region 32. Further, the tip member 34 may be attached to the first (e.g., distal) sheath 22. It can be appreciated that the tip member 34 may be designed with an atraumatic geometry, whereby the tip member 34 may include a tapered portion designed to ease navigation of the medical system 10 through challenging anatomical pathways. Additionally, FIG. 4 illustrates that the inner shaft 14 may include a lumen 36 through which a guidewire may be advanced.

It can be appreciated from FIG. 4 that as the outer shaft 12 translates with respect to the inner shaft 14, the second sheath 24 and the first sheath 22 will, correspondingly, translate with respect to one another. As will be described in greater detail below, as the outer shaft 12 and/or the inner shaft 14 are manipulated via the handle 18 (shown in FIG. 1), the second sheath 24 and/or the first sheath 22 may translate to release the medical implant 16.

Figure 5:
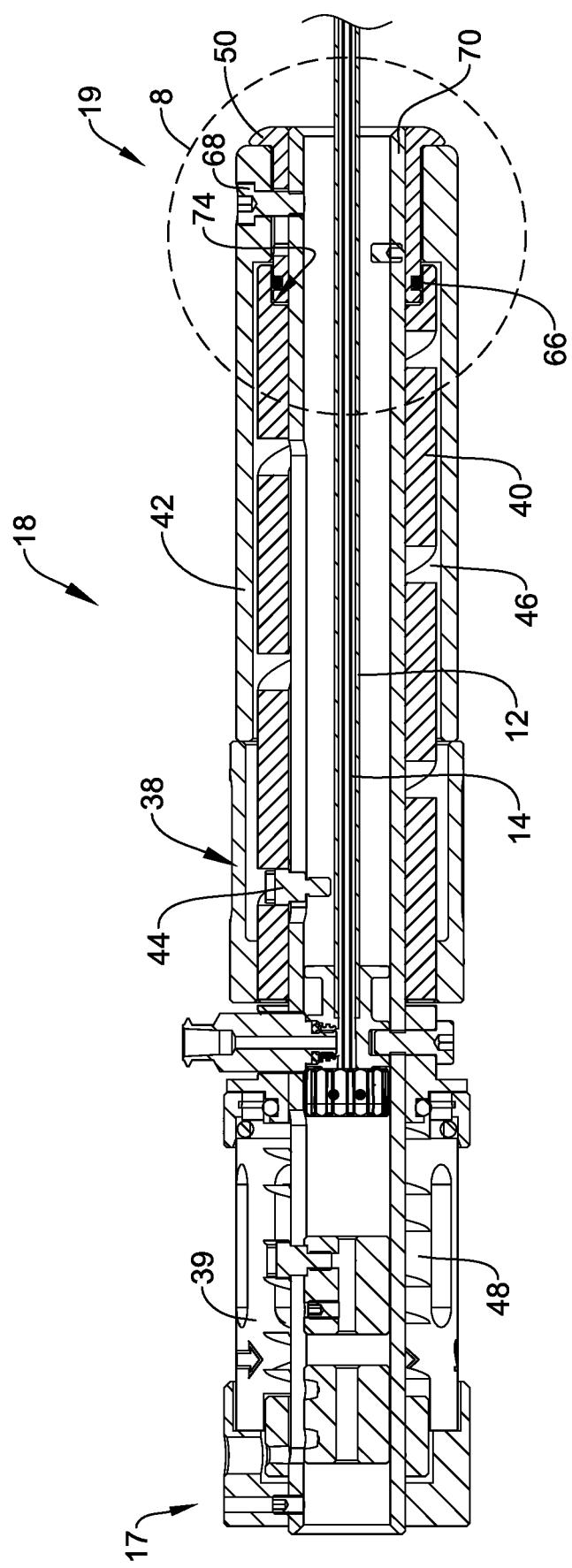
FIG. 5 is a cross-sectional view of an example handle of the medical device system shown in FIG. 1.

FIG. 5 illustrates a cross-section of the handle 18 described above. The handle 18 may include a proximal end region 17 and a distal end region 19. FIG. 5 shows the outer shaft 12 (described above) and the inner shaft 14 (described above) entering the distal end region 19 of the handle 18. The outer shaft 12 may be coupled (e.g., attached) to a translation member 44. As shown in FIG. 5, the translation member 44 may be nested within a helical channel 46 disposed along a carriage 40. The carriage 40 may be coupled (e.g., attached) to a first actuator 38. It can be appreciated that the first actuator 38 may be designed to permit an operator to grasp and rotate the first actuator 38, whereby rotation of the first actuator 38 may correspondingly rotate the carriage 40. Further, rotation of the carriage 40 may rotate the helical channel 46, thereby causing the translation member 44 to translate parallel to the longitudinal axis of the handle 18. It can be appreciated that because the translation member 44 is attached to the outer shaft 12, translation of the translation member 44 will translate the outer shaft 12 correspondingly. Further, in some examples, the first actuator 38 may be designed to rotate in both a clockwise and a counterclockwise direction, thereby permitting an operator to selectively translate the outer shaft 12 in both a distal-to-proximal direction and also a proximal-to-distal direction.

Additionally, FIG. 5 illustrates that the handle 18 may include a second actuator 39 which is coupled to the inner shaft 14. Further, it can be appreciated the second actuator 39 may be coupled to the inner shaft 14 via a similar mechanism as described with respect to the first actuator 38. For example, the second actuator 39 may be coupled to the inner shaft 14 via a second translation member and second carriage 48. Further, rotation of the second actuator 39 (either in a clockwise or a counter-clockwise direction) may translate the inner shaft 14 in a distal-to-proximal direction or a proximal-to-distal direction (depending on the direction of rotation of the second actuator 39).

Further, as discussed above, because each of the outer shaft 12 and the inner shaft 14 are coupled to the second sheath 24 (not shown in FIG. 5, but described above) and the first sheath 22 (not shown in FIG. 5, but described above), manipulation of the first actuator 38 and/or the second actuator 39 may control the movement of the first sheath 22 and the second sheath 24 relative to one another. Additionally, it can be appreciated that it may be beneficial for either the first sheath 22 (not shown in FIG. 5, but described above) or the second sheath 24 (not shown in FIG. 5, but described above) to maintain its position while the second sheath 24 or the first sheath 22 is rotated. In other words, if an operator chooses to rotate the first actuator 38 (thereby translating the second sheath 24), the handle 18 may be designed such that the second carriage 48 resists any back-loading forces placed upon it by the translation of the second sheath 24 (and/or the deployment of the medical implant). Correspondingly, if the operator chooses to rotate the second actuator 39 (thereby translating the first sheath 22), the handle 18 may be designed such that the first carriage 40 resists any back-loading forces placed upon it by the translation of the first sheath 22 (and/or the deployment of the medical implant).

It can be appreciated, therefore, that, in some configurations, each of the first carriage 40 and second carriage 48 may need to be prevented from freely rotating (e.g., freely spinning) within the handle 18. In other words, it may be beneficial to design the handle 18 to include one or more components which impart a frictional resistance to the rotation of each of the first carriage 40 and the second carriage 48. It can be appreciated that this resistance may be translated to the first actuator 38 and the second actuator 39, thereby requiring an operator to overcome the resistive force in order to rotate either of the first actuator 38 and the second actuator 39. However, this resistance may provide increased control as an operator rotates either of the first actuator 38 and the second actuator 39 (when deploying the medical implant, for example).

To that end, FIG. 5 shows that the handle 18 may include a housing 42 positioned overtop the first carriage 40. In other words, the first carriage 40 may rotate inside an inner cavity of the housing 42. Further, FIG. 5 illustrates a cap 50 positioned along the distal end region of the handle 18. Specifically, the cap 50 may extend into the distal end of the inner cavity of the housing 42 and also into at least a portion of the distal end region of the first carriage 40. Additionally, FIG. 5 illustrates that the handle 18 may include a resistance member 66 (e.g., gasket, rubber gasket, etc.) positioned along the proximal end region of the cap 50. The resistance member 66 may exert an outward radial force upon the carriage 40, thereby imparting a resistive force (as described above) to the rotation of the first carriage 40. In other words, in order to rotate the first actuator 38, an operator may have to overcome the radially outward force the resistance member 66 imparts onto the first carriage 40.

While not shown in the figures, in some examples the medical device system 10 may include a third shaft (not shown for simplicity). The third shaft may be referred to as a "middle" shaft in some examples. The third shaft may be positioned between the inner shaft 14 and the outer shaft 12. Further, the third shaft may extend from the handle 18 to a positioned adjacent the stent-valve 16 (described above). In some examples, the stent-valve 16 may be coupled to the third shaft. For example, the stent-valve 16 may be coupled to the third shaft via a stent-valve holder (not shown in the figures). Additionally, the third shaft may be stationary with respect to the outer shaft 12, the inner shaft 14 or both the outer shaft 12 and the inner shaft 14. In other words, as the outer shaft 12 and/or the inner shaft 14 are actuated (as described above), the third shaft may remain stationary relative thereto. It can be appreciated that the third shaft may provide a stable, stationary "platform" on which to mount the stent-valve 16. For example, as the first sheath 22 and/or the second sheath 24 are translating with respect to one another (and the stent-valve 16), the third shaft may prevent the stent-valve 16 from sliding (e.g., dragging) as the first sheath 22 and/or the second sheath 24 are translated.

In some examples, the third shaft (described above) may be coupled to an inner spine tube 70 (shown in FIG. 5). The inner spine tube 70 may be coupled to the housing 42 via a screw 68. It can be appreciated that the inner spine tube 70 and/or the housing 42 may remain stationary as the outer shaft 12 and/or the inner shaft 14 are actuated by the first actuator 38 and the second actuator 39, respectively.

Figure 6:
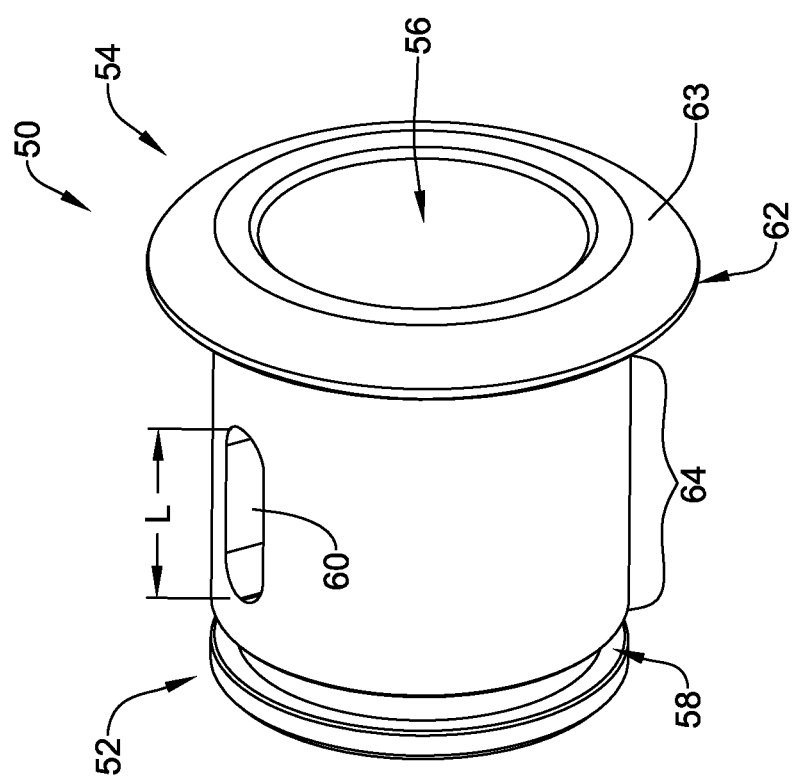
FIG. 6 is a perspective view of an example component of the medical device delivery system shown in FIG. 1.

FIG. 6 shows a perspective view of the cap 50 described above. The cap 50 may include a proximal end region 52, a distal end region 54 and a medial region 64 extending therebetween. Further, the cap 50 may include a lumen 56 extending from the proximal end region 52 to the distal end region 54. FIG. 6 further illustrates that the cap 50 may include a groove 58 (e.g., channel, etc.) positioned along the proximal end region 52 of the cap 50. The groove 58 may extend circumferentially around the outer surface of the cap 50. As will be shown in greater detail in FIG. 7, the groove 58 may extend radially inward from an outer surface of the cap 50. Further, the groove 58 may be sized to accept the resistance member 66 (not shown in FIG. 6, but described above).

FIG. 6 further illustrates that the cap 50 may include an aperture 60 positioned within the medial region 64 of the cap 50. The aperture 60 may include a length "L." In some examples, the aperture may extend longitudinally along the medial region 64. Additionally, the cap 50 may include a lip 62 positioned along the distal end region 54 of the cap 50. The lip 62 may extend circumferentially around and extend radially away from the outer surface of the cap 50. In some examples, the lip 62 may include one or more tapered and/or curved surfaces 63.

Figure 7:
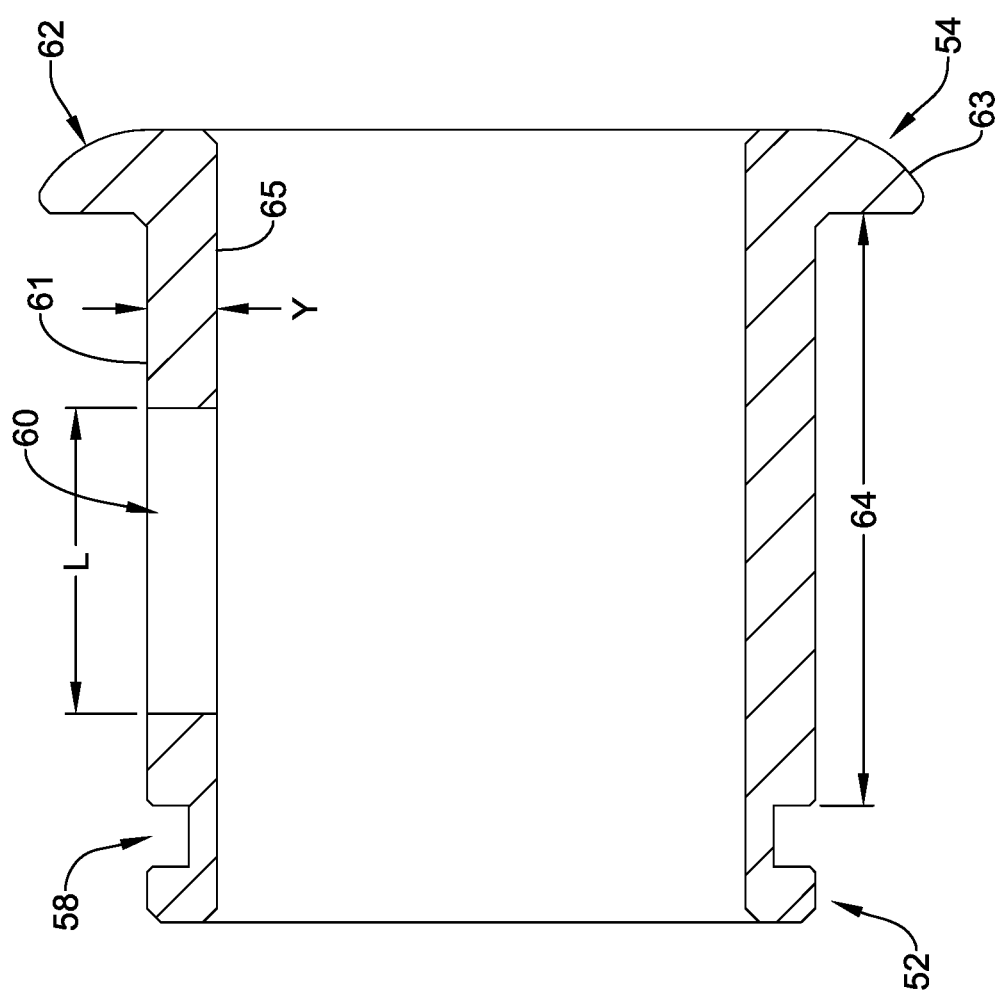
FIG. 7 is a cross-sectional view of the example component of the medical device system shown in FIG. 5.

FIG. 7 illustrates a cross section of the cap 50 shown in FIG. 6. For example, FIG. 7 illustrates the groove 58 positioned along the proximal end region 52 of the cap 50. Further, FIG. 7 illustrates that the cap may include a wall thickness "Y" extending between the outer surface 61 and the inner surface 65 of the medial region 64. As shown in FIG. 7, the groove 58 may extend only partially into the wall thickness "Y" of the cap 50.

Additionally, FIG. 7 illustrates the aperture 60 having a length "L" as described above. As shown in FIG. 7, the aperture 60 may extend entirely through the wall thickness "Y" of the cap 50. However, this is not intended to be limiting. Rather, in some examples, the aperture may extend only partially through the wall thickness "Y" of the cap 50. Further, FIG. 7 illustrates the lip 62 extending radially outward from the outer surface 61 of the cap 50. As discussed above, the lip 62 may include one or more tapered and/or curved surfaces 63.

While the resistive force imparted by the resistance member 66 (described above) may provide increased control for an operator when deploying the medical implant, in some instances it may be desirable to selectively remove the resistive force imparted by the resistance member 66 on the second sheath 24 (via the connection of the first carriage 40 and the outer shaft 12). Removing the resistive force may permit the second sheath 24 to more freely translate relative to the first sheath 22.

For example, in some instances it may be desirable for an operator to engage (e.g., load) the medical implant into the first sheath 22 and/or the second sheath 24. Further, in order to properly position the implant within the first sheath 22 and/or the second sheath 24, the operator may be required to manipulate the first sheath 22 and/or the second sheath 24 relative to one another. It can be appreciated that loading the implant into the first sheath 22 and/or the second sheath 24 may require an operator to manipulate the first actuator 38 and/or the second actuator 39 at the handle (in order to adjust the spacing and position of the first sheath 22 and/or the second sheath 24 relative to one another). It can be appreciated that this may require the operator to physically move between the handle (at one end of the medical device system 10) and the first and second sheaths 22, 24 (at the opposite end of the medical device system 10). Therefore, it may be desirable to design the handle 18 such that an operator can selectively remove the resistive force imparted to the first actuator 38 (and subsequently the second sheath 24 via the carriage 40 and outer shaft 12). In other words, when the operator is loading the stent-valve, the resistive force may be removed, and subsequently, after loading (e.g., during insertion of the medical device system 10 into a patient's body) and/or when the operator is deploying the stent-valve, the resistive force may be applied.

Figure 8:
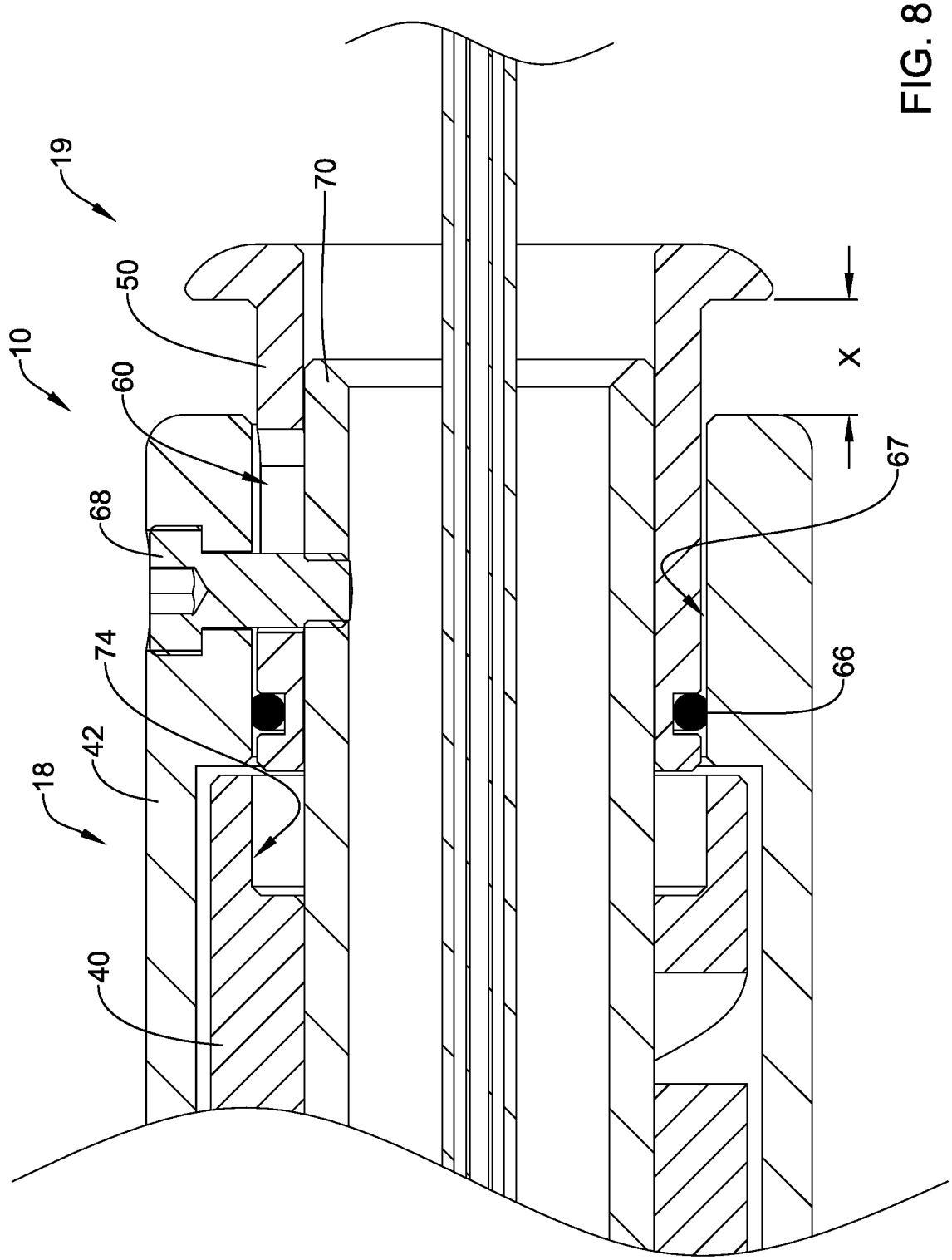
FIG. 8 is a cross-sectional view of a portion of the example handle shown in FIG. 1.

To that end, FIG. 8 illustrates a detailed view of the distal end region 19 of the medical device system 10 in a "pre-deployment" configuration. The pre-deployment configuration may represent a configuration which is designed to load the stent-valve into the first sheath 22 and/or the second sheath 24 (e.g., a configuration in which an operator can manipulate the second sheath 24 without having to use the handle 18).

FIG. 8 illustrates that the cap 50 (described above) has been shifted in a distal direction a distance "X." Further, FIG. 8 illustrates that shifting the cap 50 in a distal direction may correspondingly shift the resistance member 66 in a distal direction a distance "X." Specifically, shifting the cap 50 in a distal direction may shift the resistance member 66 to a position in which it is free from (e.g., not contacting) the inner surface 74 of the first carriage 40. As shown in FIG. 8, the resistance member 66 is positioned adjacent to an inner surface 67 of the housing 42, thereby removing the resistive force from the carriage 40.

FIG. 8 further illustrates that the handle 18 may include a screw 68 which is positioned at least partially within the aperture 60 of the cap 50. It can be appreciated that the screw 68 may be prevent the cap from sliding all the way out the distal end of the housing 42. Additionally, it can be appreciated that the length of the aperture 60 (described as length "L" in FIG. 6 and FIG. 7 corresponds to the distance "X" the cap shifts in the distal direction.

Figure 9:
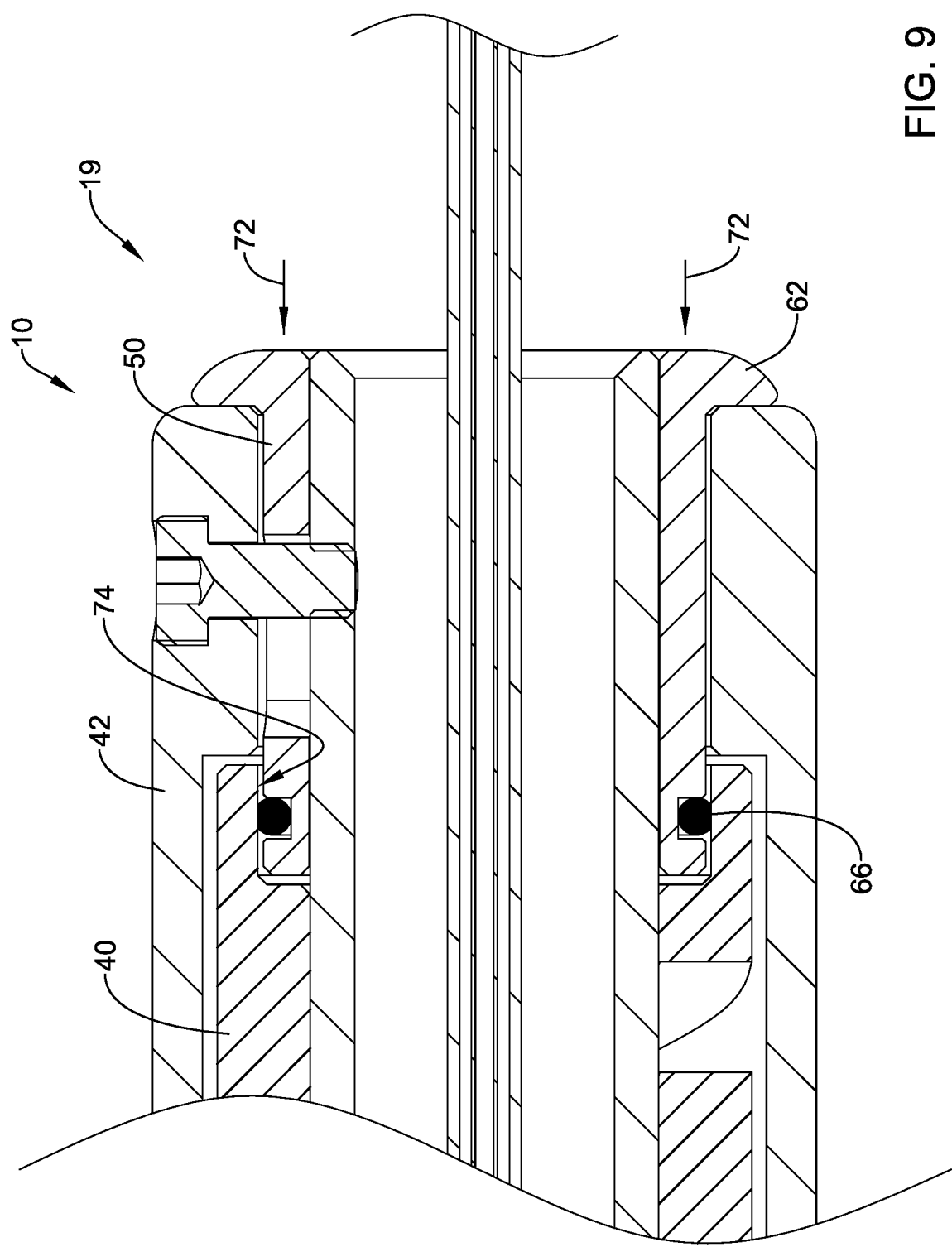
FIG. 9 is a cross-sectional view of a portion of the example handle shown in FIG. 1.

FIG. 9 illustrates a detailed view of the distal end region 19 of the medical device system 10 in a "deployment" configuration. The deployment configuration may represent a configuration which is designed to advance the system through a blood vessel and/or deploy the medical implant at a target site, for example. FIG. 9 illustrates that the cap 50 (described above) has been shifted in a proximal direction (shown by the arrows 72) such that the resistance member 66 contacts the inner surface 74 of the carriage 40. As described above, in this configuration, the resistance member 66 may exert a radially outward force upon the inner surface 74 of the carriage 40, which, in turn, imparts a resistive force on the first actuator 38 (not shown in FIG. 9) and the second sheath 24 (not shown in FIG. 9).

FIG. 9 further illustrates that the lip 62 of the cap 50 may be shifted proximally such that it contacts the distal end of the housing 42. It can be appreciated that the lip 62 may be designed to permit an operator to engage a portion thereof, which may permit the operator to more easily shift the cap 50 between the pre-deployment configuration and the deployment configuration. Further, the lip 62 may have a profile (e.g., a beveled edge) that sits flush with the housing 42, in order to reduce the exposed profile of the cap 50. This feature may reduce the risk of the cap 50 being moved accidentally out of the proximal position (after the cap 50 has been placed in the proximal position for implanting a loaded stent-valve 16).

Figure 10:
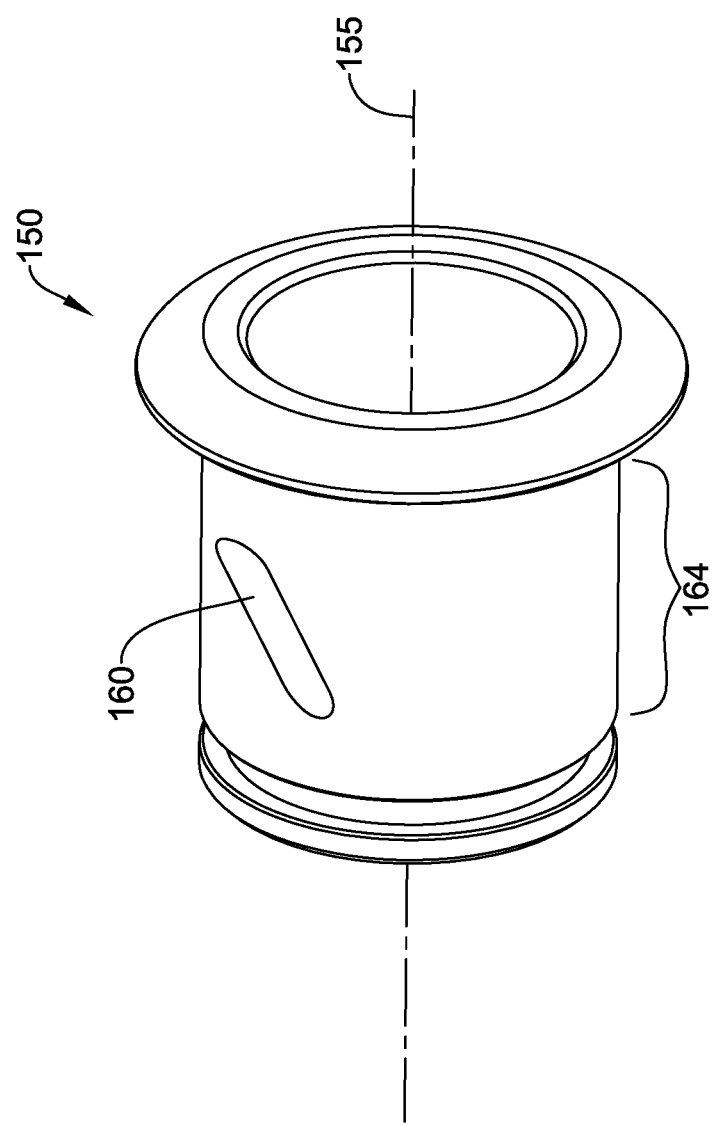
FIG. 10 is a perspective view of another example component of the medical device delivery system shown in FIG. 1.

FIG. 10 illustrates another example cap 150. The cap 150 may be similar in form and function to the cap 50. For example, FIG. 10 shows that the cap 150 may include an aperture 160 positioned in the medial region 164 of the cap 150. However, as illustrated in FIG. 10, the aperture 160 may be offset from the longitudinal axis 155 of the cap 150. It can be appreciated that offsetting the aperture 160 from the longitudinal axis 155 of the cap 150 may allow the resistance member to be shifted between the pre-deployment configuration and the deployment configuration via "rotating" the cap 150. In other words, instead of requiring an operator to slide the cap 150 linearly along the longitudinal axis (as described in FIG. 8 and FIG. 9), the cap configuration shown in FIG. 10 may allow the resistance member 66 shift longitudinally as the cap 150 is being rotated.

As discussed above, in some instances it may be desirable for an operator to engage (e.g., load) a medical implant into the first sheath 22 and/or the second sheath 24. Further, in order to properly load a medical implant within the first sheath 22 and/or the second sheath 24, the operator may be required to manipulate (e.g., shift) the first sheath 22 and/or the second sheath 24 relative to one another. Therefore, in some instances, it may be beneficial for an operator to use a medical implant loading device (e.g., stent-valve loader) to help advance the first sheath 22 and/or the second sheath 24 relative to one another to cover and contain a medical implant within the first sheath 22 and/or the second sheath 24.

Figure 11:
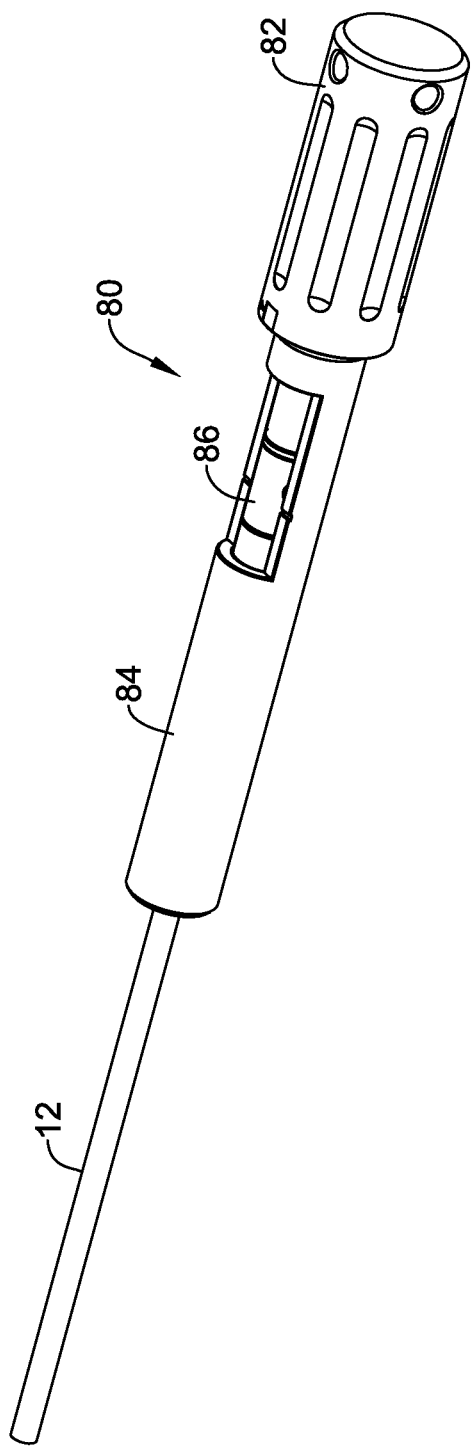
FIG. 11 is a perspective view of an example stent loading device.

FIG. 11 illustrates an example medical implant loading device 80. The medical implant loading device 80 may be utilized by an operator to load a stent-valve 16 (shown above) into the first sheath 22 and/or the second sheath 24 prior to performing a medical procedure. FIG. 11 illustrates the medical implant loading device 80 in a configuration in which the medical implant 16 has already been loaded within the medical implant loading device 80. In other words, the first sheath 22, the second sheath 24 and the medical implant 16 are not visible in FIG. 11 (as they are positioned within the medical implant loading device 80).

However, FIG. 11 does illustrate that the medical implant loading device 80 may include a knob 82 coupled to a stem 84. FIG. 11 further illustrates the outer shaft 12 (described above) extending into the stem 84. Additionally, FIG. 11 shows that the implant loading device may include a sleeve 86 (visible through an aperture located in the stem 84). As will be described in greater detail below, it can be appreciated that the knob 82 may be rotated with respect to the stem 84. Rotation of the knob 82 with respect to the stem 84 may translate the first sheath 22 (described above) longitudinally with respect to the second sheath 24 (described above).

Figure 12:
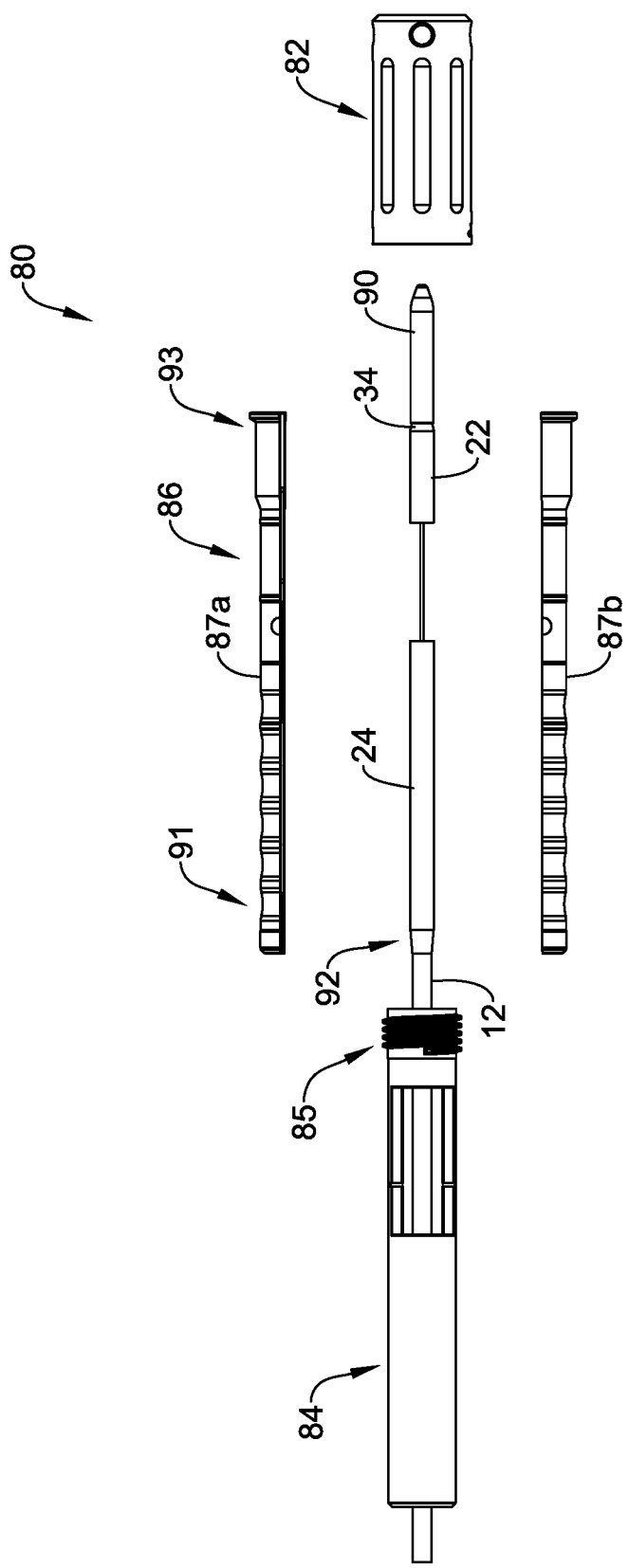
FIG. 12 is an exploded view of the example stent loading device shown in FIG. 11.

FIG. 12 illustrates an exploded view of the medical implant loading device 80 described above. For example, FIG. 12 illustrates the knob 82 and the stem 84. Further, FIG. 12 illustrates that the stem 84 may include a threaded portion 85 positioned along an end region thereof. As will be described in greater detail with respect to FIG. 13 below, the threaded portion 85 may be utilized to couple the knob 82 with the stem 84.

FIG. 12 further illustrates the sleeve 86 described above. As shown in FIG. 12, the sleeve 86 may separate into a first sleeve portion 87a and a second sleeve portion 87b. The first sleeve portion 87a and the second sleeve portion 87b may engage with one another in a "clamshell" configuration to form sleeve 86. The sleeve 86 may include proximal end region 91 and a distal end region 93. Additionally, FIG. 12 shows the outer shaft 12 extending through the stem 84. It can be appreciated that the stem 84 may be slid onto and overtop the first sheath 22 and the second sheath 24 such that the stem 84 is positioned proximal to the second sheath 24. Additionally, the sleeve 86 may be positioned within portion of an interior cavity of the stem 84 and/or the knob 82.

As described above, FIG. 12 further illustrates the outer shaft 12 coupled to the second sheath 24. In some examples, the distal end region of the outer shaft 12 may include a tapered region 92. The tapered region 92 may extend from the distal end region of the outer shaft 12 to the proximal end of the second sheath 24. Additionally, FIG. 12 illustrates the tip member 34 (described above) extending into an extension member 90. The extension member 90 may extend in a proximal-to-distal direction from the tip member 34.

As discussed above, the medical implant loading device 80 may be utilized to load a medical device (e.g., a stent-valve) into the first sheath 22 and/or the second sheath 24. The medical implant loading device 80 may be configured to apply an axial force to the first sheath 22 and/or the second sheath 24 as part of the loading operation. These axial forces may be designed to urge movement of the first sheath 22 and/or the second sheath 24 toward one another to cover all, or a portion of, the stent-valve 16. As discussed above, it can be appreciated that the ability to release the resistance of the first actuator 38 and/or the second actuator 39 (described above) within the handle (for example, by moving the cap 50 to its distal position as described above) may allow the first actuator 38 and/or the second actuator 39 to move freely as the knob 82 and/or the stem 84 are rotated (and, therefore, axially translated) with respect to one another. It can be appreciated that permitting the first actuator 38 and/or the second actuator 39 to move freely as the knob 82 shifts relative to the stem 84 may facilitate the loading of the stent-valve 16 (illustrated in FIGS. 1-4) by permitting the operator to remain at the distal end of the catheter, rather than having to physically move repeatedly between the handle and the distal end of the catheter to "mirror" the relative movement of the first sheath 22 and the second sheath 24 with the first actuator 38 and the second actuator 39.

Figure 13:
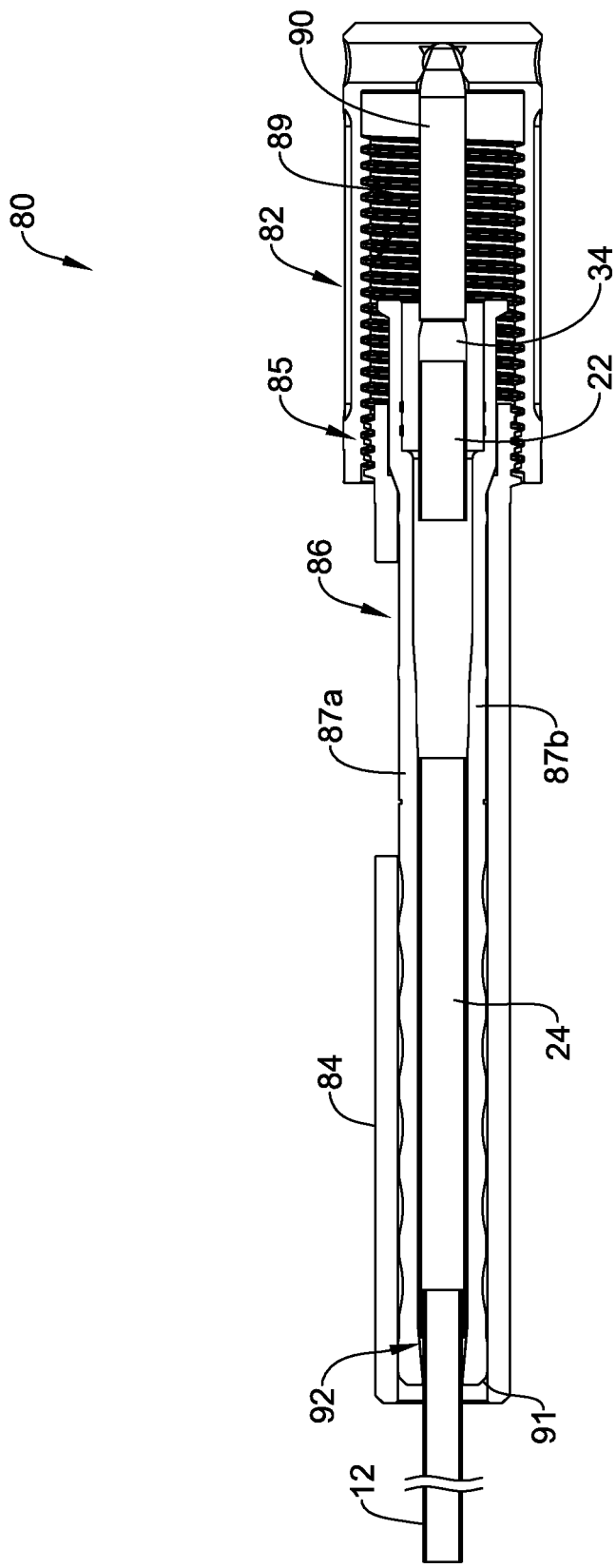
FIG. 13 is a cross-sectional view of the example stent loading device shown in FIG. 11.

FIG. 13 illustrates a cross-section of the medical implant loading device 80. For simplicity, FIG. 13 does not show a medical implant positioned between the first sheath 22 and the second sheath 24. However, it can be appreciated that an operator may position the medical implant (e.g., a stent-valve 16) between the first sheath 22 and the second sheath 24 prior to moving the first sheath 22 relative to the second sheath 24 via the medical implant loading device 80. As described above, in some instances the medical implant may be coupled to a third shaft (described above), whereby the third shaft may extend between the first sheath 22 and the second sheath 24.

It can be appreciated from FIG. 13 that rotation of the knob 82 may apply a proximally-directed force to the first sheath 22 (via the extension member 90). For example, the knob 82 may include an inner surface profile which engages the extension member 90. Further, FIG. 13 illustrates that the knob 82 may include a threaded portion 89 designed to mate with the threaded portion 85 along the distal end region of the stem 84.

FIG. 13 shows that the extension member 90 may abut (directly or indirectly) the tip member 34 (or any other member attached to the tip member 34) of the first sheath 22. Further, it can be appreciated from FIG. 13 that rotation of the stem 84 may apply a distally-directed force to the second sheath 24 via sleeve 86. FIG. 13 illustrates that the sleeve 86 (including the first sleeve portion 87*a* and the second sleeve portion 87*b*) may be positioned within the stem 84. Further, the second sheath 24 and all (or a portion of) the first sheath 22 may be positioned within the sleeve 86. Additionally, FIG. 13 illustrates that the distal end region 91 of the sleeve 86 may include a (e.g. tapered) surface which engages the tapered portion 92 of the outer shaft 12.

As described above, an operator may rotate either the knob 82 and/or the stem 84 to progressively apply an axially compressive force between the knob 82 and the stem 84 to move the first sheath 22 and/or the second sheath 24 closer toward one another. This may permit an operator to load a stent-valve into the first sheath 22 and/or the second sheath 24 while working primarily at the distal end of the catheter. The medical implant loading device 80 may apply the axial forces at the distal end to close the first sheath 22 and/or the second sheath 24 over the stent valve as part of the loading operation. As described above, it can be appreciated that the ability to release the resistance of the first actuator 38 and/or the second actuator 39 within the handle 18 (by shifting the cap 50 to its distal position, for example) and may improve the speed and efficiency in which an operator may load a medical implant prior to performing a medical procedure.

The materials that can be used for the various components of the medical devices and/or systems disclosed herein may include those commonly associated with medical devices. For simplicity purposes, the following discussion makes reference to the medical device delivery system 10 including the various components of the medical device delivery system 10.

The medical device delivery system 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high density polyethylene (HDPE), polyester, Marlex high-density polyethylene, Marlex low-density polyethylene, linear low density polyethylene (for example REXELL®), ultra-high molecular weight (UHMW) polyethylene, polypropylene, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device delivery system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the shaft in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device delivery system 10 to achieve the same result.

In some embodiments, a degree of Magnetic Resonance Imaging (MRI) compatibility is imparted into the shaft. For example, the medical device delivery system 10 may include a material that does not substantially distort the image and create substantial artifacts (e.g., gaps in the image). Certain ferromagnetic materials, for example, may not be suitable because they may create artifacts in an MRI image. The medical device delivery system 10 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery system for an implantable medical device, comprising:
    an outer shaft having a distal end region, a proximal end region and a lumen extending therebetween;
    a handle coupled to the proximal end region of the outer shaft, wherein the handle includes a first actuator, a carriage and a housing,
    a cap coupled to the handle; and
    a resistance member disposed along a portion of the cap;
    wherein the cap is configured to shift between a first configuration and a deployment configuration, and wherein the carriage is free from the resistance member in the first configuration and wherein the resistance member contacts the carriage in the deployment configuration;
    wherein the resistance member contacts an inner surface along a distal end region of the housing in the first configuration.

2. The delivery system of claim 1, wherein the resistance member contacts an inner surface along a distal end region of the carriage in the deployment configuration.

3. The delivery system of claim 1, wherein the carriage is configured to rotate, and wherein the resistance member is configured to increase a rotational force required to rotate the carriage in the deployment configuration.

4. The delivery system of claim 1, wherein the cap includes a circumferential groove positioned along a proximal end region thereof, wherein at least a portion of the resistance member is positioned along the groove.

5. The delivery system of claim 1, further comprising an implant loading device positioned adjacent the distal end region of the outer shaft.

6. The delivery system of claim 5, wherein the cap includes an inner surface, an outer surface and a wall extending therebetween, and wherein the cap includes an aperture extending through a wall of the cap.

7. The delivery system of claim 6, wherein the aperture includes a length, and wherein the length of the aperture corresponds to a distance along which the cap shifts between the first configuration and the deployment configuration.

8. The delivery system of claim 6, wherein the aperture is aligned along a longitudinal axis of the cap.

9. The delivery system of claim 6, wherein the aperture is offset from a longitudinal axis of the cap.

10. The delivery system of claim 9, wherein rotating the cap shifts it between the first configuration and the deployment configuration.

11. The delivery system of claim 1, wherein the cap includes a circumferential lip extending circumferentially along a distal end region thereof.

12. The delivery system of claim 11, wherein the lip extends radially away from an outer surface of the cap.

13. The delivery system of claim 1, wherein the resistance member is configured to exert a radially outward force on an inner surface of the carriage in the deployment configuration.

14. A delivery system for an implantable medical device, comprising:
    an outer shaft having a distal end region, a proximal end region and a lumen extending therebetween;
    a handle coupled to the proximal end region of the outer shaft, wherein the handle includes a first actuator, a carriage and a housing;
    a cap coupled to the handle; and
    a resistance member disposed along a portion of the cap,
    wherein the cap is configured to shift between a first configuration and a deployment configuration, and wherein the carriage is free from the resistance member in the first configuration and wherein the resistance member exerts a radially outward force upon the carriage in the deployment configuration;
    wherein the resistance member contacts an inner surface along a distal end region of the housing in the first configuration.

15. The delivery system of claim 14, wherein the resistance member contacts an inner surface along a distal end region of the carriage in the deployment configuration.

16. The delivery system of claim 14, wherein the carriage is configured to rotate, and wherein the resistance member is configured to increase a rotational force required to rotate the carriage in the deployment configuration.

17. A method of manufacturing an implantable medical device, the method comprising:
    engaging the implantable medical device with a medical device delivery system in a pre-deployment configuration, the medical device delivery system including:
        an outer shaft having a distal end region, a proximal end region and a lumen extending therebetween;
        a handle coupled to the proximal end region of the outer shaft, wherein the handle includes a first actuator, a carriage and a housing;
        a cap coupled to the handle; and a resistance member disposed along a portion of the cap, wherein the resistance member contacts an inner surface along a distal end region of the housing in the pre-deployment configuration;

converting the medical device delivery system from the pre-deployment configuration to a deployment configuration, wherein converting the medical device delivery system includes shifting the cap from a first position to a second position, wherein the carriage is free from the resistance member when the cap is in the first position and wherein the resistance member contacts the carriage when the cap is in the second position.

18. The method of claim 17, wherein the implantable medical device includes an implantable heart valve.

\* \* \* \* \*